(12) United States Patent
Ishizuka et al.

(10) Patent No.: US 9,603,928 B2
(45) Date of Patent: Mar. 28, 2017

(54) MEDICINAL COMPOSITION FOR PROMOTING SYNTHESIS OF PROTOPORPHYRIN IX

(71) Applicants: SBI Pharmaceuticals Co., Ltd., Tokyo (JP); Osaka City University, Osaka (JP)

(72) Inventors: Masahiro Ishizuka, Tokyo (JP); Urara Oto, Tokyo (JP); Atsuko Kamiya, Tokyo (JP); Kiwamu Takahashi, Tokyo (JP); Tohru Tanaka, Tokyo (JP); Toshiyuki Ozawa, Osaka (JP); Kuniyuki Morimoto, Osaka (JP); Keitaro Watanabe, Tokyo (JP)

(73) Assignees: SBI Pharmaceuticals Co., Ltd., Tokyo (JP); Osaka City University, Osaka (JP)

( * ) Notice: Subject to any disclaimer, the term of this patent is extended or adjusted under 35 U.S.C. 154(b) by 0 days.

(21) Appl. No.: 14/898,581

(22) PCT Filed: Jun. 13, 2014

(86) PCT No.: PCT/JP2014/065813
§ 371 (c)(1),
(2) Date: Dec. 15, 2015

(87) PCT Pub. No.: WO2014/203833
PCT Pub. Date: Dec. 24, 2014

(65) Prior Publication Data
US 2016/0136274 A1 May 19, 2016

(30) Foreign Application Priority Data
Jun. 19, 2013 (JP) ................................. 2013-129057

(51) Int. Cl.
| | |
|---|---|
| *A61K 31/195* | (2006.01) |
| *A61K 41/00* | (2006.01) |
| *A61K 45/06* | (2006.01) |
| *A61K 31/197* | (2006.01) |
| *A61K 31/198* | (2006.01) |
| *A61K 31/375* | (2006.01) |
| *A61K 33/40* | (2006.01) |
| *A61K 31/16* | (2006.01) |
| *A61K 31/194* | (2006.01) |

(52) U.S. Cl.
CPC .......... *A61K 41/0061* (2013.01); *A61K 31/16* (2013.01); *A61K 31/194* (2013.01); *A61K 31/197* (2013.01); *A61K 31/198* (2013.01); *A61K 31/375* (2013.01); *A61K 33/40* (2013.01); *A61K 45/06* (2013.01)

(58) Field of Classification Search
CPC .................................................. A61K 31/195

USPC ......................................................... 514/566
See application file for complete search history.

(56) References Cited

U.S. PATENT DOCUMENTS

| 5,895,786 A * | 4/1999 | Ben-Hur .............. A61K 31/195 |
| | | 514/185 |
| 2008/0254013 A1 | 10/2008 | Angst et al. |
| 2013/0131184 A1 | 5/2013 | Kusuda |
| 2013/0231299 A1 | 9/2013 | Angst et al. |

FOREIGN PATENT DOCUMENTS

| JP | H07-133277 | 5/1995 |
| JP | 2000-510123 A | 8/2000 |
| JP | 2008-501664 A | 1/2008 |
| JP | 2012-31067 A | 2/2012 |
| WO | WO2014203833 | 12/2014 |

OTHER PUBLICATIONS

International Search Report corresponding to PCT/JP2014/065813, mailed Sep. 16, 2014, 4 pages.
Junpei Saito et al., "W2-3 Tazai Taisei Ryokunokin ni Taisuru Pheophorbide a-Na o Mochiita PDT no Yukosei no Tsuite", *The Journal of Japan Society for Laser Surgery and Medicine*, Jul. 2007, vol. 28, No. 2, pp. 211, paragraph of 'Method', paragraph of 'Result'.
Junpei Saito et al., Ippan Endai 5 'PDT no Rinsho to Kiso 3', "O5-5 Tazai Taisei Ryokunokin (MDRP) ni Taisuru Pheophorbide a-Na o Mochiita PDT Koka", *The Journal of Japan Society for Laser Surgery and Medicine*, 2007, vol. 28, No. 3, pp. 319, paragraph of 'Method' paragraph of 'Result'.
Lee, C.F., et al., "delta-Aminolaevulinic acid-mediated photodynamic antimicrobial chemotherapy on Pseudomonas aeruginosa planktonic and biofilm cultures", *J. Photochem. Photobiol. B: Biology*, Jul. 19, 2004, vol. 75, No. 1-2, pp. 21-25, Abstract, Fig. 2, 3.
Wardlaw, J.L., et al., "Photodynamic therapy against common bacteria causing wound and skin infections", *Vet. J.*, Jun. 2012, vol. 192, No. 3, pp. 374-377, Abstract, p. 375, right column, paragraph of 'P. aeruginosa', fig. 1.
Oka, Yoko, "In vitro combined effects of antibacterial agents against clinically isolated multiple-drug resistant *Pseudomonas aeruginosa* (MDRP) strains", *Japanese Journal of Chemotherapy*, Japanese Society of Chemotherapy, Aug. 2005, vol. 53, No. 8, pp. 476-482.

(Continued)

*Primary Examiner* — Yong Chu
*Assistant Examiner* — Sonya Wright
(74) *Attorney, Agent, or Firm* — Myers Bigel, P.A.

(57) ABSTRACT

The object of the present invention is to elucidate the resistance mechanism in infections that show resistance to ALA-PDT that uses a single ALA, and to provide a novel treatment method against these infections. The present invention provides a pharmaceutical composition for promoting protoporphyrin IX production in ALA-PDT for treating infection, characterized in that it comprises a substance that promotes the conversion from coproporphyrinogen III to protoporphyrin IX.

5 Claims, 1 Drawing Sheet

(56) References Cited

OTHER PUBLICATIONS

Extended European Search Report corresponding to European Patent Application No. EP 14814295.3, Dated Jan. 30, 2017; 8 pages.
Smetana Z et al: "Treatment of Viral Infections With 5-Aminolevulinic Acid and Light", Lasers in Surgery and Medicine, Wiley-Liss, New York, US, vol. 21, Jan. 1, 1997, pp. 351-358.

* cited by examiner

MEDICINAL COMPOSITION FOR PROMOTING SYNTHESIS OF PROTOPORPHYRIN IX

STATEMENT OF PRIORITY

This application is a 35 U.S.C. §371 national phase application of International Application Serial No. PCT/JP2014/065813, filed Jun. 13, 2014, which claims the benefit, under 35 U.S.C. §119 (a) of Japanese Patent Application No. 2013-129057, filed Jun. 19, 2013, the entire contents of each of which are incorporated by reference herein.

TECHNICAL FIELD

The present invention relates to a pharmaceutical composition for promoting protoporphyrin IX production in ALA-PDT for treating infection.

BACKGROUND ART

Photodynamic therapy (PDT) is a treatment method in which a photosensitizer is administered to a subject and utilizes the cytotoxicity of reactive oxygen species including singlet oxygens produced by photoexcitation. PDT has been gathering attention in recent years, owing to the fact that it is a treatment method that is non-invasive and has less tendency of leaving a therapeutic scar.

On the other hand, 5-aminolevulinic acids (also referred to herein as "ALAs") are a type of natural amino acids comprised in vivo that exist widely in animals or plants or fungi. Although ALAs do not have light sensitivity per se, protoporphyrin IX (hereinafter also referred to as "PpIX") which is the form metabolically activated by a group of a series of enzymes in the heme biosynthetic pathway in cells is known as a photosensitizer possessing peaks at 410 nm, 510 nm, 545 nm, 580 nm, 630 nm, etc. Accordingly, the research of 5-aminolevulinic acids-photodynamic therapy (hereinafter also referred to as "ALA-PDT") in which administration of ALM and PDT is carried out in combination to a subject has been brought forward.

Research employing ALA-PDT for treating infection has recently been conducted, and has been gathering attention as an infection treatment method that does not employ an antibiotic (Non-Patent Literature 1). However, the present inventors found that among pathogenic microorganisms that are the cause of infections, there are some which show resistance to ALA-PDT that uses a single ALA. Particularly in *Pseudomonas aeruginosa*, it was found that those which show resistance to ALA-PDT that uses a single ALA include multi-drug resistant *Pseudomonas aeruginosa* (MDRP). In other words, the present inventors presented a novel problem in ALA-PDT for treating infection. However, the mechanism in which pathogenic microorganisms show resistance to ALA-PDT has thus far never been elucidated, and this has been the bottleneck to solve this problem.

Numerous occurrences of infection by MDRP have been reported in medical institutions. MDRP is reported to infect those with reduced immunity e.g. due to use of an immunosuppressing agent or acquired immunodeficiency syndrome (AIDS), those that have exhausted physical strength due to e.g. long-term hospitalization or surgery, elderly who are bedridden, and the like to cause severe symptoms, and this has been an extremely large social problem.

A method to use two or more antibiotics in combination to perform infection treatment by synergistic and additive effects thereof has been investigated for these problems (Non-Patent Literature 2). Moreover, numerous researches for finding novel derivatives such as a carbapenem derivative which have superior antibiotic activity against MDRP are also being carried out (Patent Literature 1). However, an effective method for treating infection by MDRP has not yet been established, and prevention of infection has been the main countermeasure.

Moreover, even if an effective antibiotic or a combination of antibiotics against MDRP is developed in the future, the emergence of *Pseudomonas aeruginosa* that show further resistance to these agents is inevitably predicted. For the above reasons, development of a novel method for treating MDRP that does not rely solely on antibiotics has been strongly demanded.

CITATION LIST

[Patent Literature 1] Japanese Published Unexamined Patent Application Publication No. Hei 7-133277
[Non-Patent Literature 1] Chia-Fen Lee, Chi-Jui Lee, Chin-Tin Chen, Ching-Tsan Huang, "d-Aminolaevulinic acid mediated photodynamic antimicrobial chemotherapy on *Pseudomonas aeruginosa* planktonic and biofilm cultures," Journal of Photochemistry and Photobiology B:Biology. Vol. 75, pp 21-25 (2004).
[Non-Patent Literature 2] Yoko Oka, "Effect of combination use of antibiotics against multi-drug resistant *Pseudomonas aeruginosa*," Japanese Journal of Chemotherapy, Japanese Society of Chemotherapy, August 2005, Vol. 53, No. 8, p. 476-482

SUMMARY OF THE INVENTION

Problems to be Solved by the Invention

The object of the present invention is to elucidate the resistance mechanism in infections that show resistance to ALA-PDT that uses a single ALA, and to provide a novel treatment method against these infections.

Means for Solving the Problems

As described above, the present inventors found for the first time that there are infections that show resistance to ALA-PDT that uses a single ALA. In particular, it was found that infections that show resistance to ALA-PDT that uses a single ALA include multi-drug resistant *Pseudomonas aeruginosa*. In other words, the present inventors presented for the first time an extremely important medical and public health problem in ALA-PDT for treating infection.

The present inventors carried out extensive investigation of the resistance mechanism of infections that show resistance to ALA-PDT that uses a single ALA in order to solve the above problems. As a result, it was surprisingly found that when ALAs are applied to pathogenic microorganisms that are the causes of such infections, most of ALAS that are incorporated in the aforementioned microorganisms are not converted into protoporphyrin IX (PpIX) which is the point of action of ALA-PDT, and metabolization is ceased at its precursor coproporphyrinogen III (CPIII). In other words, the present inventors found out for the first time that this phenomenon is in fact the reason that some infections show resistance to ALA-PDT (see Example 1 herein).

Next, based on the above knowledge, the present inventors carried out extensive exploration of the substance that promotes the metabolization from CPIII to PpIX. As a result, it was surprisingly found that the conversion from CPIII to PpIX can be promoted by combining administration of a given substance (such as a chelating agent, hydrogen peroxide, or an ascorbic acid) to a subject with ALA-PDT, and ALA-PDT can also be effectively applied to infections that show resistance to ALA-PDT that uses a single ALA, thus completing the present invention (see Examples 2 and 3 herein).

In other words, the present invention relates to a pharmaceutical composition for promoting protoporphyrin IX production in ALA-PDT for treating infection, characterized in that it comprises a substance that promotes the conversion from coproporphyrinogen III to protoporphyrin IX.

Here, one embodiment of the present invention is characterized in that said "substance that promotes the conversion from coproporphyrinogen III to protoporphyrin IX" is selected from the group consisting of a chelating agent, hydrogen peroxide, and an ascorbic acid.

Moreover, one embodiment of the present invention is characterized in that said chelating agent is selected from the group consisting of an aminopolycarboxylic acid chelating agent, a hydroxycarboxylic acid chelating agent, deferoxamine, deferasirox, and deferiprone.

Moreover, one embodiment of the present invention is characterized in that said aminopolycarboxylic acid chelating agent is selected from the group consisting of ethylenediaminetetraacetic acid (EDTA), ethylenediaminediacetic acid, hydroxyethylethylenediaminetriacetic acid (HEDTA), dihydroxyethylethylenediaminetetraacetic acid (DHEDDA), nitrilotriacetic acid (NTA), hydroxyethyliminodiacetic acid (HIDA), N-(2-hydroxyethyl) iminodiacetic acid, β-alaninediacetic acid, cyclohexanediaminetetraacetic acid, nitrilotriacetic acid, iminodiacetic acid, N-(2-hydroxyethyl) iminodiacetic acid, diethylenetriaminepentaacetic acid (DTPA), N-(2-hydroxyethyl)ethylenediaminetriacetic acid, glycol ether diaminetetraacetic acid, glutamic acid diacetic acid, aspartic acid diacetic acid, methylglycine diacetic acid, iminodisuccinic acid, serine diacetic acid, hydroxyiminodisuccinic acid, dihydroxyethylglycine, aspartic acid, glutamic acid, and triethylenetetramine-N,N,N',N'', N''',N'''-hexaacetic acid, as well as pharmaceutically acceptable salts thereof.

Moreover, one embodiment of the present invention is characterized in that said hydroxycarboxylic acid chelating agent is selected from the group consisting of malic acid, citric acid, glycolic acid, gluconic acid, heptonic acid, tartaric acid, and lactic acid, as well as pharmaceutically acceptable salts thereof.

Moreover, one embodiment of the present invention is characterized in that said infection treatment is a treatment for infections that show resistance to ALA-PDT that uses a single ALA.

Moreover, one embodiment of the present invention is characterized in that said infection is *Pseudomonas aeruginosa* infection.

Moreover, one embodiment of the present invention is characterized in that said *Pseudomonas aeruginosa* infection is multi-drug resistant *Pseudomonas aeruginosa* infection.

Moreover, one embodiment of the present invention is characterized in that said multi-drug resistant *Pseudomonas aeruginosa* infection is *Pseudomonas aeruginosa* infection that shows resistance to at least a fluoroquinolone antibiotic, a carbapenem antibiotic, and an aminoglycoside antibiotic.

Another embodiment of the present invention provides a method for promoting protoporphyrin IX production in ALA-PDT for treating infection in a subject, characterized in administering a therapeutically effective amount of a substance that promotes the conversion from coproporphyrinogen III to protoporphyrin IX to the subject.

Another embodiment of the present invention provides a combination medicine for treating *Pseudomonas aeruginosa* infection that shows resistance to ALA-PDT that uses a single ALA, comprising sequentially or simultaneously administered (1) ALAS and (2) a substance selected from the group consisting of a chelating agent, hydrogen peroxide, and an ascorbic acid.

Moreover, one embodiment of the present invention is characterized in that an aspect of said combination in said combination medicine is a combination drug.

Moreover, one embodiment of the present invention is characterized in that an aspect of said combination in said combination medicine is a kit.

Another embodiment of the present invention provides a method for treating *Pseudomonas aeruginosa* infection in a subject, characterized in sequentially or simultaneously administering to the subject (1) ALAs and (2) a substance selected from the group consisting of a chelating agent, hydrogen peroxide, and an ascorbic acid.

An invention that is any combination of one or more characteristics of the present invention described above is also encompassed in the scope of the present invention.

Effects of the Invention

According to the present invention, treatment for infections that show resistance to ALA-PDT that uses a single ALA can be performed. In particular, according to the present invention, treatment of MDRP infection of which an effective treatment method has thus far not been found will be possible. In other words, the present invention is an invention of extreme importance in medical science.

Because the infection treatment method according to the present invention is a treatment method with a completely different mechanism from an infection treatment method by an antibiotic, there is no need to be concerned about emergence of drug resistant bacteria. In other words, according to the treatment method of the present invention, the problem of emergence of drug resistant bacteria that is currently a large social problem can be avoided. In other words, the present invention is also an invention of extreme importance in terms of public health.

Moreover, the infection treatment according to the present invention and an infection treatment by an antibiotic can also be used in combination. For example, a greater therapeutic effect can be achieved by using treatment methods of two different mechanisms in combination (i.e., the infection treatment according to the present invention and an infection treatment by an antibiotic) in a patient of an infection that shows severe symptoms and requires emergency treatment.

In particular, according to the present invention, *Pseudomonas aeruginosa* infection treatment can be performed regardless of whether *Pseudomonas aeruginosa* is MDRP or not. Accordingly, when *Pseudomonas aeruginosa* infection is treated in a patient at a medical institution, the emergence of MDRP in the patient can be prevented by treating the patient with the present invention without determining whether the pathogenic bacteria is MDRP or not. Moreover, symptoms can be forestalled from becoming more severe if by any chance the pathogenic bacteria of *Pseudomonas aeruginosa* infection were MDRP.

Further, the symptoms becoming more severe by MDRP infection is largely reported in those with reduced immunity e.g. due to use of an immunosuppressing agent or acquired immunodeficiency syndrome (AIDS), those that have exhausted physical strength due to e.g. long-term hospitalization or surgery, elderly who are bedridden, and the like. On the other hand, because ALA-PDT is a non-invasive treatment method, it can be said to be a preferred treatment method for subjects with reduced immunity as described above or patients with reduced physical strength. Moreover, ALAS are substances that are highly safe in human body, and there are less concerns of drug allergy etc. compared to administration of antibiotics. Moreover, the method of administering ALAS to the patient can be selected depending on the condition or symptoms of the patient such as application, ingestion, and the like. In other words, the present invention happens to provide a treatment method particularly appropriate for patients with high risk of symptoms by MDRP infection becoming more severe.

DESCRIPTION OF EMBODIMENTS

ALAs as used herein refer to an ALA or a derivative thereof, or salts thereof.

ALA as used herein means a 5-aminolevulinic acid. ALA is also referred to as 6-aminolevulinic acid, and is a type of amino acid.

The compound represented by the following Formula (I) can be exemplified as an example of an ALA derivative. In Formula (I), $R^1$ represents a hydrogen atom or an acyl group, and $R^2$ represents a hydrogen atom, a linear or branched alkyl group, a cycloalkyl group, an aryl group, or an aralkyl group. Note that in Formula (I), ALA corresponds to when $R^1$ and $R^2$ are hydrogen atoms.

[Chemical Formula 1]

$$R^1\text{—NHCH}_2\text{COCH}_2\text{CH}_2\text{COOR}^2 \quad (I)$$

ALAS may act as an active ingredient in vivo in the form of the ALA of Formula (I) or a derivative thereof, and can be administered as a prodrug (precursor) that is degraded by an in vivo enzyme.

The acyl group in $R^1$ of Formula (I) can include a linear or branched alkanoyl group having 1-8 carbons such as formyl, acetyl, propionyl, butyryl, isobutyryl, valeryl, isovaleryl, pivaloyl, hexanoyl, octanoyl, and benzylcarbonyl groups, and an aroyl group having 7-14 carbons such as benzoyl, 1-naphthoyl, and 2-naphthoyl groups.

The alkyl group in $R^2$ of Formula (I) can include a linear or branched alkyl group having 1-8 carbons such as methyl, ethyl, propyl, isopropyl, butyl, isobutyl, sec-butyl, tert-butyl, pentyl, isopentyl, neopentyl, hexyl, heptyl, and octyl groups.

The cycloalkyl group in $R^2$ of Formula (I) can include a cycloalkyl group having 3-8 carbons which may be saturated or have partially unsaturated bonds, such as cyclopropyl, cyclobutyl, cyclopentyl, cyclohexyl, cycloheptyl, cyclooctyl, cyclododecyl, and 1-cyclohexenyl groups.

The aryl group in $R^2$ of Formula (I) can include an aryl group having 6-14 carbons such as phenyl, naphthyl, anthryl, and phenanthryl groups.

The aralkyl group in $R^2$ of Formula (I) can be exemplified with the same aryl groups as above as the aryl moiety and the same alkyl groups as above as above as the alkyl moiety, and can specifically include an aralkyl group having 7-15 carbons such as benzyl, phenethyl, phenylpropyl, phenylbutyl, benzhydryl, trityl, naphthylmethyl, and naphthylethyl groups.

Preferred ALA derivatives include compounds where $R^1$ is a formyl group, an acetyl group, a propionyl group, a butyryl group, and the like. Moreover, preferred ALA derivatives also include compounds where the above $R^2$ is a methyl group, an ethyl group, a propyl group, a butyl group, a pentyl group, and the like. Moreover, preferred ALA derivatives also include compounds where the combination of the above $R^1$ and $R^2$ is each combination of (formyl and methyl), (acetyl and methyl), (propionyl and methyl), (butyryl and methyl), (formyl and ethyl), (acetyl and ethyl), (propionyl and ethyl), and (butyryl and ethyl).

Among ALAs, a salt of an ALA or a derivative thereof can include a pharmaceutically acceptable acid addition salt, a metal salt, an ammonium salt, an organic amine addition salt, and the like. Acid addition salts can be exemplified by e.g. each of inorganic acid salts such as a hydrochloride salt, a hydrobromide salt, a hydroiodide salt, a phosphate salt, a nitrate salt, and a sulfate salt, and each of organic acid addition salts such as a formate salt, an acetate salt, a propionate salt, a toluenesulfate salt, a succinate salt, an oxalate salt, a lactate salt, a tartrate salt, a glycolate salt, a methanesulfonate salt, a butyrate salt, a valerate salt, a citrate salt, a fumarate salt, a maleate salt, and a malate salt. Metal salts can be exemplified by each of alkali metal salts such as a lithium salt, a sodium salt, and a potassium salt, each of alkaline earth metal salts such as a magnesium salt and a calcium salt, and each of metal salts such as aluminum and zinc. Ammonium salts can be exemplified by alkyl ammonium salts such as an ammonium salt and a tetramethylammonium salt. Organic amine salts can be exemplified by each of salts such as a triethylamine salt, a piperidine salt, a morpholine salt, and a toluidine salt. Note that these salts can also be employed as a solution at the time of use.

Among the above ALAs, the most favorable are ALA and various esters such as an ALA methyl ester, an ALA ethyl ester, an ALA propyl ester, an ALA butyl ester, and an ALA pentyl ester, as well as hydrochloride salts, phosphate salts, and sulfate salts thereof. In particular, an ALA hydrochloride salt and an ALA phosphate salt can be exemplified as particularly favorable.

The above ALAs can be manufactured by e.g. well-known methods such as chemical synthesis, production by microorganisms, and production by enzymes. Moreover, the above ALAs may also form a hydrate or a solvate, and ALAs can be employed alone or in an appropriate combination of two or more.

When the above ALAs are to be prepared as an aqueous solution, attention must be paid so that the aqueous solution will not become alkaline in order to prevent degradation of ALAs. In the case it becomes alkaline, degradation can be prevented by removing oxygen.

ALA-PDT as used herein means photodynamic therapy (PDT) that employs ALAs, most typically PDT that employs ALA.

The above ALA-PDT is a method employed for therapeutic agents for infections that utilizes the fact that when performing PDT which is administering a compound that reacts to light and irradiating light to treat the target site, ALAs which do not have a photosensitization effect per se is administered, PpIX induced via the pigment biosynthetic pathway is allowed to accumulate in the pathogenic microorganism of the infection, the PpIX accumulated in the microorganism is excited to allow photoexcitation of the surrounding oxygen molecules, and singlet oxygens produced as a result have a cytotoxic effect due to their intense oxidative power. The wavelength of the light for exciting the above PpIX is preferably 400 nm-700 nm.

A "substance that promotes the conversion from coproporphyrinogen III to protoporphyrin IX" as used herein means in particular a substance that directly or indirectly promotes the conversion from coproporphyrinogen III to protoporphyrin IX in the metabolic pathway of ALAs in vivo.

Examples of "a substance that promotes the conversion from coproporphyrinogen III to protoporphyrin IX" as used herein can include, but are not limited to, a chelating agent, hydrogen peroxide, and an ascorbic acid.

A chelating agent as used herein refers to a substance that binds to (coordinates with) a metal ion by possessing a ligand that has multiple coordination loci (multidentate ligand).

Examples of the above chelating agent can include a aminopolycarboxylic acid chelating agent, an aromatic or aliphatic carboxylic acid chelating agent, an amino acid chelating agent, an ether carboxylic acid chelating agent, a phosphonic acid chelating agent, a hydroxycarboxylic acid chelating agent, a polyelectrolyte (including olygomer electrolyte) chelating agent, a polyalcohol, a nitrogen-containing chelating agent such as dimethylglyoxime, a sulfur-containing chelating agent such as thioglycolic acid, deferoxamine, deferasirox, deferiprone, and the like.

The form of these chelating agents is arbitrary. In case of an acid chelating agent, it may be in a free acid form, or may be in the form of a salt such as a sodium salt, a potassium salt, and an ammonium salt. Further, these may be in ester derivative forms thereof that are hydrolyzable.

Although it is not limiting, an aminopolycarboxylic acid chelating agent, a hydroxycarboxylic acid chelating agent, deferoxamine, deferasirox, and/or, deferiprone can be favorably employed as the chelating agent in the present invention.

Examples of an aminopolycarboxylic acid chelating agent can include ethylenediaminetetraacetic acid (EDTA), ethylenediaminediacetic acid, hydroxyethylethylenediaminetriacetic acid (HEDTA), dihydroxyethylethylenediaminetetraacetic acid (DHEDDA), nitrilotriacetic acid hydroxyethyliminodiacetic acid (HIDA), N-(2-hydroxyethyl)iminodiacetic acid, β-alaninediacetic acid, cyclohexanediaminetetraacetic acid, nitrilotriacetic acid, iminodiacetic acid, N-(2-hydroxyethyl)iminodiacetic acid, diethylenetriaminepentaacetic acid (DTPA), N-(2-hydroxyethyl)ethylenediaminetriacetic acid, glycol ether diaminetetraacetic acid, glutamic acid diacetic acid, aspartic acid diacetic acid, methylglycine diacetic acid, iminodisuccinic acid, serine diacetic acid, hydroxyiminodisuccinic acid, dihydroxyethylglycine, aspartic acid, glutamic acid, and triethylenetetramine-N,N,N',N'',N''',N'''-hexaacetic acid, as well as salts and derivatives thereof such as esters.

Examples of a hydroxycarboxylic acid chelating agent can include malic acid, citric acid, glycolic acid, gluconic acid, heptonic acid, tartaric acid, and lactic acid, as well as salts and derivatives thereof.

For deferoxamine, salts and derivatives thereof can also be employed, although in particular deferoxamine mesylate is favorably employed. Deferoxamine mesylate is sometimes also referred to as desferal. Because deferoxamine mesylate is approved for administration in vivo (such as administration by injection), it can be favorably employed in the present invention e.g. when directly administering a chelating agent in vivo. Since deferasirox and deferiprone are also approved for administration in vivo (such as oral administration), then can be favorably employed in the present invention e.g. when directly administering a chelating agent in vivo.

In the present invention, the chelating agent may be composed of one compound, or two or more compounds may be used in combination.

An "ascorbic acid" as used herein is a concept that comprises an ascorbic acid or a derivative thereof, or a salt thereof, and is also referred to as vitamin C. Moreover, although L-ascorbic acid is the naturally-occurring form, either one of L-ascorbic acid and D-ascorbic acid which is obtained by chemical synthesis can be favorably used in the present invention.

The disease to be the subject of ALA-PDT employing the present invention is not particularly limited as long as it is an infection such as bacterial infection, fungal infection, viral infection, parasitic infection, and it is in particular favorably employed for bacterial infection. Bacterial infections to which ALA-PDT employing the pharmaceutical composition of the present invention can be favorably employed can include *Staphylococcus aureus* infection or *Pseudomonas aeruginosa* infection.

"ALA-PDT that uses a single ALA" as used herein means that no substance other than ALAs that has an influence on the effect of ALA-PDT is employed in ALA-PDT.

An infection "shows resistance to ALA-PDT that uses a single ALA" means that even when ALA-PDT that uses a single ALA is applied to the causative pathogen of the aforementioned infection, there is almost no change in the number of bacteria compared to when the experiment was performed under the same conditions except that PDT was not performed. For example, it may mean that even when ALA-PDT that uses a single ALA (e.g. wavelength 410 nm, 50 J/cm$^2$) is applied to the causative pathogen of the aforementioned infection, 10% or more of the number of bacteria survives compared to when the experiment was performed under the same conditions except that PDT was not performed.

A multi-drug resistant *Pseudomonas aeruginosa* (MDRP) as used herein means *Pseudomonas aeruginosa* that shows resistance to at least a fluoroquinolone antibiotic (such as ciprofloxacin and levofloxacin), a carbapenem antibiotic (such as imipenem and meropenem), and an aminoglycoside antibiotic (such as amikacin). In other words, *Pseudomonas aeruginosa* that shows resistance to at least one of fluoroquinolone antibiotics, at least one of carbapenem antibiotics, and at least one of aminoglycoside antibiotics is to be encompassed in the "multi-drug resistant *Pseudomonas aeruginosa*" in the present invention.

Confirmation that the subject *Pseudomonas aeruginosa* is MDRP can be made by e.g. confirming that the minimal inhibitory concentration (MIC) of the subject *Pseudomonas aeruginosa* is amikacin 32 μg/ml, imipenem 16 μg/ml, and ciprofloxacin ≥4 μg/ml, respectively.

When performing ALA-PDT employing the present invention, the administration of ALAs to a subject and the administration of "a substance that promotes the conversion from coproporphyrinogen III to protoporphyrin IX" may be at the same or different times. In other words, ALAS may be administered to the subject first, and then "a substance that promotes the conversion from coproporphyrinogen III to protoporphyrin IX" may be administered, or vice versa.

When performing ALA-PDT employing the present invention, the method for administering ALM can include oral administration including sublingual administration, intravenous injection including infusion, and transdermal administration by e.g. poultices, suppositories, and applicable solution types. Among these, transdermal or oral administration is preferred, and transdermal administration by application can be favorably exemplified with respect to efficiency and convenience. The dosage form of the therapeutic agent in oral administration dosage form can include powders, granules, tablets, capsules, syrups, suspensions, and the like, the therapeutic agent in intravenous injection dosage form can include injections, infusions, and the like. Moreover, the dosage form of the therapeutic agent in transdermal administration form can include solution types, water-soluble ointment-dissolved types, cream types, jelly-dissoluted types, spray types, and the like. For example, the transdermal administration method by applicable solution types can specifically include the method of contacting a liquid retention material sufficiently containing the ALAs solution such as a gauze or an absorbent cotton with skin infected with *Pseudomonas aeruginosa*. The dosage of ALAs may be an amount where the accumulated amount of PpIX in the subject microorganism is an amount effective for ALA-PDT. The specific dosages of ALAS are, for example, in case of oral administration, 1 mg-1000 mg, preferably 5 mg-100 mg, more preferably 10 mg-30 mg, and further preferably 15 mg-25 mg per kilogram of body weight in ALA equivalency, and in case of transdermal administration by applicable solution types, the concentration of ALM solution is 1% by weight-90% by weight, preferably 2% by weight-40% by weight, and more preferably 10% by weight-20% by weight in ALA equivalency. Moreover, when ALAS is used in the solution form, it is preferred that attention is paid for preparation so that the aqueous solution will not become alkaline in order to prevent degradation of ALM. In the case it becomes alkaline, degradation of the active ingredient can be prevented by removing oxygen.

When performing ALA-PDT employing the present invention, the method for administering "a substance that promotes the conversion from coproporphyrinogen III to protoporphyrin IX" can include oral administration including sublingual administration, intravenous injection including infusion, and transdermal administration by e.g. poultices, suppositories, and applicable solution types. The method for administering a chelating agent and an ascorbic acid can include oral administration including sublingual administration, intravenous injection including infusion, and transdermal administration by e.g. poultices, suppositories, and applicable solution types. The method for administering hydrogen peroxide can include intravenous injection including infusion, and transdermal administration by e.g. poultices, suppositories, and applicable solution types. The dosage form of the therapeutic agent in oral administration dosage form can include powders, granules, tablets, capsules, syrups, suspensions, and the like, the therapeutic agent in intravenous injection dosage form can include injections, infusions, and the like. Moreover, the dosage form of the therapeutic agent in transdermal administration form can include solution types, water-soluble ointment-dissoluted types, cream types, jelly-dissoluted types, spray types, and the like. For example, the transdermal administration method by applicable solution types can specifically include the method of contacting a liquid retention material sufficiently containing "a substance that promotes the conversion from coproporphyrinogen III to protoporphyrin IX" such as a gauze or an absorbent cotton with skin infected with *Pseudomonas aeruginosa*.

When performing ALA-PDT employing the present invention, the method for administering ALAS and the method for administering "a substance that promotes the conversion from coproporphyrinogen III to protoporphyrin IX" may be the same or different. For example, ALAS may be orally administered to the subject, and "a substance that promotes the conversion from coproporphyrinogen III to protoporphyrin IX" may be transdermally administered.

The subject of the treatment method according to the present invention is typically a human, but also includes non-human animals such as pet animals, laboratory animals, and farm animals. Moreover, when not desirable, humans can be excluded from the subject.

A "combination medicine" as used herein means a medicine of a combination of two or more substances or composition, in which the aspect of the combination thereof is not limited.

As used herein, the aspect of the combination of (1) ALAS and (2) a substance selected from the group consisting of a chelating agent, hydrogen peroxide, and an ascorbic acid is a "combination drug" means that as one embodiment of the combination medicine according to the present invention, each of the substances are formulated in the same composition in order to simultaneously administer (1) and (2).

As used herein, the aspect of the combination of (1) ALM and (2) a substance selected from the group consisting of a chelating agent, hydrogen peroxide, and an ascorbic acid is a "kit" means that as one embodiment of the combination medicine according to the present invention, (1) and (2) are separately prepared. In such an aspect, because (1) and (2) are separately prepared, (1) and (2) can be sequentially or simultaneously administered to a subject.

As used herein, "simultaneously administering" (1) ALAs and (2) a substance selected from the group consisting of a chelating agent, hydrogen peroxide, and an ascorbic acid comprises e.g. administering a composition that simultaneously comprises (1) and (2) to a subject, such as when the aspect of the combination of (1) and (2) is a combination drug. Moreover, it also comprises simultaneously administering separately prepared (1) and (2), such as when the aspect of the combination of (1) and (2) is a kit.

As used herein, "sequentially administering" (1) ALAS and (2) a substance selected from the group consisting of a chelating agent, hydrogen peroxide, and an ascorbic acid as comprises e.g. administering separately prepared (1) and (2) at a separate timing, such as when the aspect of the combination of (1) and (2) is a kit.

Other optional ingredients such as other medicinal ingredients, nutrients, and carriers can be added as necessary to the pharmaceutical composition or the combination medicine according to the present invention. For example, as optional ingredients, various compounding ingredients for the preparation of drugs such as pharmaceutically acceptable ordinary carriers, binders, stabilizers, solvents, dispersion mediums, expanders, excipients, diluents, pH buffers, disintegrants, solubilizers, solubilizers, and isotonic agents, such as crystalline cellulose, gelatin, lactose, starch, magnesium stearate, talc, vegetable and animal fat, oil, gum, and polyalkylene glycol can be added.

When treating, an infection with the present invention, well-known antibiotics may be used in combination. Because it is thought that the mechanisms of the antibiotic effect by well-known antibiotics and the infection-treating effect by the present invention are fundamentally different, an additive or in some cases a synergistic effect can be expected.

The terms used herein, except for those that are particularly defined, are employed for describing particular embodiments, and do not intend to limit the invention.

Moreover, the term "comprising" as used herein, unless the content clearly indicates to be understood otherwise, intends the presence of the described items (such as components, steps, elements, and numbers), and does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having meanings consistent with the meanings herein and in related technical fields, and shall not be construed as having idealized or excessively formal meanings.

The present invention will now be described in further detail with reference to Examples. However, the present invention can be embodied by various aspects, and shall not be construed as being limited to the Examples described herein.

EXAMPLES

Example 1

Multi-drug resistant *Pseudomonas aeruginosa* (MDRP: ATCC BAA-2110) was placed in tryptic soy broth medium (TBS: from DIFCO), and cultured at 37° C. for 24 hours. With an absorptiometer, the TBS medium comprising the cultured MDRP was adjusted to $1 \times 10^9$ CFU (Colony forming unit)/ml. In a 12-well plate, the following solutions (1)-(3) were each prepared and cultured. (1): TBS medium comprising MDRP adjusted to $1 \times 10^9$ CFU/ml, (2): a solution of (1) and ALA added to a final concentration of 0.5 mg/ml, and (3): a solution of (1) and ALA added to a final concentration of 0.5 mg/ml and EDTA added to a final concentration of 400 mg/ml. The solutions were collected 4 hours after the start of culture, and suspended in 0.25 ml of PBS per 1 g of the pelleted bacteria. To 0.2 ml of the suspension, 0.01 ml of 50% acetic acid and 0.9 ml of DMF/IPA (100:1) were added, vortexed, and separated by centrifugation (14, 000 rpm, 5 min, 4° C.). The concentrations of coproporphyrinogen III (CPIII) and protoporphyrin IX (PpIX) in the supernatant after centrifugal separation were measured with HPLC. The HPLC measurement results are shown in Table 1.

As shown in Table 1, in the group where ALA was administered alone to MDRP (i.e. (2)), the proportion of PpIX against CPIII was approximately 5.5% (=(49.0/889.6)×100), which was similar to the proportion in the group where ALA was not administered to MDRP (i.e. (1)), approximately 4.7% (=(19.7/422.2)×100). In other words, it was surprisingly found that ALA incorporated into MDRP was barely converted into PpIX which is the point of action of ALA-PDT, and metabolization is almost ceased at its precursor CPIII.

Further, in the group where ALA and EDTA were administered to MDRP (i.e. (3)), the proportion of PpIX against CPIII increased to approximately 30.6% (=(233.1/764.8)×100). In other words, it was surprisingly found that the conversion from CPIII to PpIX in MDRP can be promoted by adding ALA and EDTA to MDRP.

TABLE 1

| Sample | CPIII (nM) | PpIX (nM) |
|---|---|---|
| (1) MDRP | 422.2 | 19.7 |
| (2) MDRP + ALA | 889.6 | 49.0 |
| (3) MDRP + ALA + EDTA | 764.8 | 233.1 |

Example 2

Multi-drug resistant *Pseudomonas aeruginosa* (MDRP: ATCC BAA-2110) was cultured for 24 hours at 37° C. with tryptic soy broth medium (TBS: from DIFCO). Then, the TBS medium comprising MDRP at $1 \times 10^9$ CFU/ml was dispensed in a 12-well plate at 1 ml per well, and ALA was added to a final concentration of 1 mg/ml and EDTA was added to a final concentration of 400 mg/ml. These were divided into the group subjected to PDT (PDT group) and the group not subjected to PDT (non-PDT group) (each n=1). For the control group, only ALA at a final concentration of 1 mg/ml was added to 1 ml of the TBS medium comprising MDRP at $1 \times 10^9$ CFU/ml, and PDT was not carried out. The control group and the non-PDT group were cultured for 18 hours, and the number of bacteria in each well was counted. The PDT group was cultured for 18 hours, irradiated with LED (410 nm) at 50 J/cm$^2$, and then the number of bacteria was counted.

Figure 1:
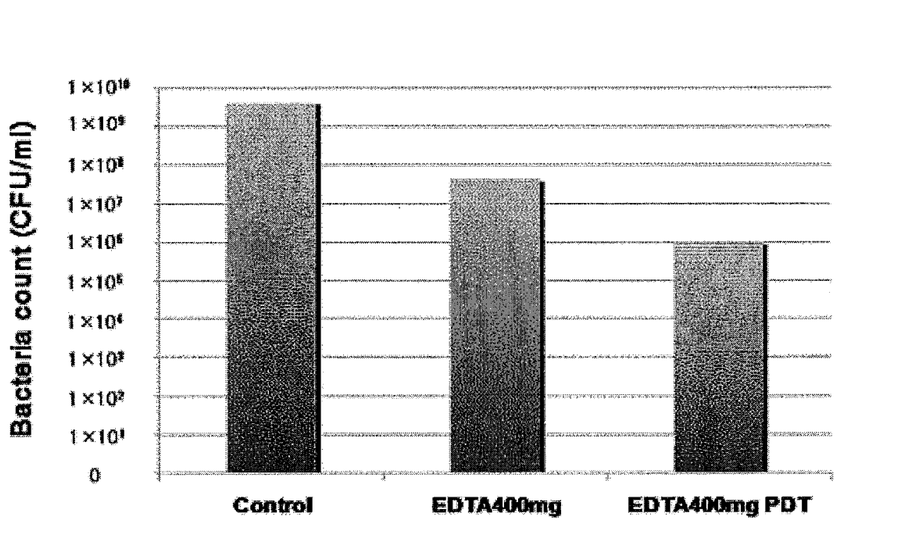
FIG. 1 is a graph that compares the number of MDRP bacteria after treatment between the group where ALA and EDTA are added and PDT is carried out on MDRP (PDT group) and the group where ALA and EDTA are added and PDT is not carried out on MDRP (non-PDT group).

As shown in FIG. 1 and Table 2, the number of bacteria in the control group after 18 hours of culture was $4.2 \times 10^9$ CFU/ml. In the non-PDT group, the number of bacteria only decreased to $4.42 \times 10^7$. On the other hand, in the PDT group, the number of bacteria surprisingly decreased to $0.94 \times 10^7$ CFU/ml. In other words, in the PDT group which is one embodiment of the present invention, the number of bacteria decreased by approximately 99.98% compared to the control group, and the number of bacteria decreased by approximately 97.9% even compared to the non-PDT group. From the above results, it was found that MDRP can be extremely efficiently decreased by carrying out PDT together with the addition of ALA and EDTA.

TABLE 2

| | Bacterial count (CFU/ml) |
|---|---|
| Control | $4.2 \times 10^9$ |
| EDTA 400 mg | $4.42 \times 10^7$ |
| EDTA 400 mg PDT | $0.94 \times 10^6$ |

Example 3

Multi-drug resistant *Pseudomonas aeruginosa* (MDRP: BAA-2110) was cultured in tryptic soy broth medium (TBS: from DIFCO) for 24 hours at 37° C. Next, the TBS medium comprising MDRP was dispensed in a 12-well dish at 1 ml per well ($1 \times 10^4 - 2 \times 10^5$ CFU/ml). ALA at a final concentration of 1 mg/ml and a chelating agent other than EDTA (2.5 mg/mL of citric acid, 2.5 mg/mL of malic acid, 1 mg/mL of diethylenetriaminepentaacetic acid (DTPA), 1 mg/mL of triethylenetetramine-N,N,N',N'',N''',N'''-hexaacetic acid, 1 mg/mL of N-(2-hydroxyethyl) iminodiacetic acid, and 1 mg/mL of deferoxamine mesylate, each at final concentration) were added to each dish. For the control group, only ALA at a final concentration of 1 mg/ml was added to 1 ml of the TBS medium comprising MDRP. Next, these were cultured for 5 hours, and the number of bacteria in each well was counted. The PDT group was cultured for 5 hours, and then irradiated with LED (410 nm) at 50 J/cm$^2$, after which the number of bacteria was counted, and further the number of bacteria at 19 hours after irradiation was also counted.

As shown in Table 3, it was confirmed that the number of bacteria significantly decreased when 1 mg/ml of ALA and various chelating agents were added to MDRP and then subjected to LED irradiation (PDT). In other words, it was also found that MDRP can also be significantly decreased by using chelating agents other than EDTA in combination with PDT.

TABLE 3

|  | Irradiation (Yes or No) | At the time of culture (CFU/mL) | 5 hours after addition of ALA + chelating agent (CFU/mL) | 19 hours after irradiation (CFU/mL) |
|---|---|---|---|---|
| control (n = 4) | No | $5.7 \times 10^4$ | $3.6 \times 10^5$ | $1.4 \times 10^9$ |
| ALA + citric acid 2.5 mg/mL (n = 2) | No | $3.8 \times 10^4$ | $4.4 \times 10^4$ | $1.7 \times 10^9$ |
| ALA + citric acid 2.5 mg/mL (n = 3) | Yes | $7.3 \times 10^4$ | $3.8 \times 10^3$ | $6.4 \times 10^2$ |
| ALA + malic acid 2.5 mg/mL (n = 2) | No | $1.2 \times 10^5$ | $1.6 \times 10^5$ | $3.2 \times 10^7$ |
| ALA + malic acid 2.5 mg/mL (n = 3) | Yes | $8.5 \times 10^4$ | $2.3 \times 10^3$ | $7.3 \times 10^1$ |
| ALA + DT 1 mg/mL (n = 3) | No | $6.3 \times 10^4$ | $6.1 \times 10^4$ | $5.7 \times 10^8$ |
| ALA + DT 1 mg/mL (n = 4) | Yes | $6.5 \times 10^4$ | $4.3 \times 10^4$ | $2.1 \times 10^2$ |
| ALA + TT 1 mg/mL (n = 3) | No | $6.3 \times 10^4$ | $8.5 \times 10^4$ | $1.5 \times 10^6$ |
| ALA + TT 1 mg/mL (n = 4) | Yes | $6.5 \times 10^4$ | $1.3 \times 10^3$ | $9.0 \times 10^1$ |
| ALA + HI 1 mg/mL (n = 3) | No | $6.3 \times 10^4$ | $1.1 \times 10^5$ | $2.2 \times 10^9$ |
| ALA + HI 1 mg/mL (n = 4) | Yes | $6.5 \times 10^4$ | $4.3 \times 10^3$ | $3.3 \times 10^2$ |
| ALA + Defe 1 mg/mL (n = 3) | No | $5.3 \times 10^4$ | $3.7 \times 10^5$ | $3.1 \times 10^9$ |
| ALA + Defe 1 mg/mL (n = 4) | Yes | $5.7 \times 10^4$ | $3.8 \times 10^2$ | $2.0 \times 10^1$ |

Numeric values in the table are average values
DT: diethylenetriaminepentaacetic acid
TT: triethylenetetramine-N,N,N',N',N",N''',N'''-hexaacetic acid
HI: N-(2-hydroxyethyl) iminodiacetic acid
Defe: deferoxamine mesylate (Desferal)

The invention claimed is:

1. A method for treating a *Pseudomonas aeruginosa* infection in a subject in need thereof, comprising sequentially or simultaneously administering to the subject a therapeutically effective amount of (1) aminolevulinic acids (ALAs) and (2) a substance selected from the group consisting of a chelating agent, hydrogen peroxide, and an ascorbic acid.

2. The method according to claim 1, wherein said chelating agent is selected from the group consisting of an aminopolycarboxylic acid chelating agent, a hydroxycarboxylic acid chelating agent, deferoxamine, deferasirox, and deferiprone.

3. The method according to claim 2, wherein said aminopolycarboxylic acid chelating agent is selected from the group consisting of ethylenediaminetetraacetic acid (EDTA), ethylenediaminediacetic acid, hydroxyethylethylenediaminetriacetic acid (HEDTA), dihydroxyethylethylenediaminetetraacetic acid (DHEDDA), nitrilotriacetic acid (NTA), hydroxyethyliminodiacetic acid (HIDA), N-(2-hydroxyethyl)iminodiacetic acid, β-alaninediacetic acid, cyclohexanediaminetetraacetic acid, nitrilotriacetic acid, iminodiacetic acid, N-(2-hydroxyethyl)iminodiacetic acid, diethylenetriaminepentaacetic acid (DTPA), N-(2-hydroxyethyl)ethylenediaminetriacetic acid, glycol ether diaminetetraacetic acid, glutamic acid diacetic acid, aspartic acid diacetic acid, methylglycine diacetic acid, iminodisuccinic acid, serine diacetic acid, hydroxyiminodisuccinic acid, dihydroxyethylglycine, aspartic acid, glutamic acid, and triethylenetetramine-N,N,N',N",N''',N'''-hexaacetic acid, as well as pharmaceutically acceptable salts thereof.

4. The method according to claim 2, wherein said hydroxycarboxylic acid chelating agent is selected from the group consisting of malic acid, citric acid, glycolic acid, gluconic acid, heptonic acid, tartaric acid, and lactic acid, as well as pharmaceutically acceptable salts thereof.

5. The method according to claim 4, wherein said *Pseudomonas aeruginosa* infection shows resistance to a 5-aminolevulinic acids-photodynamic therapy that uses a single 5-aminolevulinic acid (ALA).

* * * * *

UNITED STATES PATENT AND TRADEMARK OFFICE
CERTIFICATE OF CORRECTION

PATENT NO. : 9,603,928 B2
APPLICATION NO. : 14/898581
DATED : March 28, 2017
INVENTOR(S) : Ishizuka et al.

It is certified that error appears in the above-identified patent and that said Letters Patent is hereby corrected as shown below:

In the Specification

Column 8, Line 54: Please correct "amikacin 32 µg/ml, imipenem 16 µg/ml," to read -- amikacin ≥32 µg/ml, imipenem ≥16 µg/ml, --

Column 9, Lines 21, 29, 66: Please correct "ALAS" to read -- ALAs --
      Lines 26, 32: Please correct "ALM" to read -- ALAs --

Column 10, Lines 2, 16, 40: Please correct "ALAS" to read -- ALAs --
      Line 23: Please correct "ALM" to read -- ALAs --

Column 12, Line 31: Please correct "4.42×10'" to read -- $4.42 \times 10^7$ --
      Line 32: Please correct "0.94×10'" to read -- $0.94 \times 10^6$ --

Signed and Sealed this
Fifth Day of December, 2017

Joseph Matal
*Performing the Functions and Duties of the
Under Secretary of Commerce for Intellectual Property and
Director of the United States Patent and Trademark Office*